(12) United States Patent
Guenther

(10) Patent No.: US 9,249,473 B2
(45) Date of Patent: Feb. 2, 2016

(54) COMPOSITIONS AND METHODS FOR THE IDENTIFICATION OF INHIBITORS OF RETROVIRAL INFECTION

(71) Applicant: Trana Discovery, Inc., Cary, NC (US)

(72) Inventor: Richard H. Guenther, Cary, NC (US)

(73) Assignee: Trana Discover, Inc., Cary, NC (US)

( * ) Notice: Subject to any disclaimer, the term of this patent is extended or adjusted under 35 U.S.C. 154(b) by 0 days.

(21) Appl. No.: 13/916,335

(22) Filed: Jun. 12, 2013

(65) Prior Publication Data

US 2014/0121124 A1    May 1, 2014

Related U.S. Application Data

(63) Continuation of application No. 12/677,819, filed as application No. PCT/US2008/076210 on Sep. 12, 2008, now abandoned.

(60) Provisional application No. 61/080,092, filed on Jul. 11, 2008, provisional application No. 60/972,595, filed on Sep. 14, 2007.

(51) Int. Cl.
*C12Q 1/68* (2006.01)
*C12Q 1/70* (2006.01)
*C12N 9/99* (2006.01)

(52) U.S. Cl.
CPC *C12Q 1/703* (2013.01); *C12N 9/99* (2013.01); *C12N 2740/10011* (2013.01); *C12N 2740/16011* (2013.01); *C12Q 2600/136* (2013.01)

(58) Field of Classification Search
None
See application file for complete search history.

*Primary Examiner* — James Martinell
(74) *Attorney, Agent, or Firm* — Andrews Kurth LLP; David Bradin

(57) ABSTRACT

Methods of identifying inhibitors of retroviral propagation, tRNA used in the methods, and kits, including the tRNA, which can be used in the methods, are disclosed. Methods of treating or preventing retroviral infections by administering an effective amount of the inhibitors, and pharmaceutical compositions including the inhibitors, are also disclosed. The methods involve forming a mixture comprising a linear sequence of a tRNA anticodon stem loop fragment that is not capable of forming a stem-loop, a target nucleic acid molecule capable of binding to the tRNA anticodon stem loop fragment, and a test compound. The mixture is incubated under conditions that allow binding of the tRNA anticodon stem loop fragment and the target nucleic acid molecule in the absence of the test compound. Assays can then be performed that detect whether or not the test compound inhibits the binding of the tRNA anticodon stem loop fragment and the target nucleic acid molecule.

22 Claims, 7 Drawing Sheets

COMPOSITIONS AND METHODS FOR THE IDENTIFICATION OF INHIBITORS OF RETROVIRAL INFECTION

CROSS-REFERENCE TO RELATED APPLICATIONS

This application is a continuation of, and claims priority to, U.S. patent application Ser. No. 12/677,819, filed Mar. 11, 2010, which in turn claims priority under 35 U.S.C. 371 to PCT/US08/76210, filed on Sep. 12, 2008, which in turn claims the benefit under 35 USC 119 of U.S. Provisional Patent Application Nos. 60/972,595, filed Sep. 14, 2007, and 61/080,092, filed Jul. 11, 2008. The disclosures of said U.S. patent application Ser. No. 12/677,819, PCT/US08/76210, and U.S. Provisional Patent Application Nos. 60/972,595 and 61/080,092 are hereby incorporated herein by reference, in their respective entirety, for all purposes.

FIELD

The invention generally relates to compositions and methods of identification of inhibitors of retroviral infection and replication.

BACKGROUND

The primate lentiviruses include the human immunodeficiency viruses types 1 and 2 (HIV-1 and HIV-2) and simian immunodeficiency viruses (SIVs) (Barre-Sinoussi, F., et al. (1983) Science 220:868-871; Clavel, F. (1987) AIDS 1:135-140; Daniel, M. D., et al. (1985) Science 228:1201-1204; Desrosiers, R. C. (1990) Ann. Rev. Immunol. 8: 557-578; Gallo, R. C, et al. (1984) Science 224:500-503). HIV-1 and HIV-2 infect humans, HIV-1-like viruses infect chimpanzees, and SIV variants infect African monkeys. Humans infected by HIV-1 and HIV-2 and Asian macaques infected by certain SIV strains often develop life-threatening immunodeficiency due to depletion of CD4-positive T lymphocytes (Fauci, A., et al. (1984) Ann. Int. Med. 100:91-106; Letvin, N. L., et al. (1985) Science 230:71-739, 19).

In humans, HIV infection causes Acquired Immunodeficiency Syndrome (AIDS), an incurable disease in which the body's immune system breaks down leaving the victim vulnerable to opportunistic infections, e.g., pneumonia and certain cancers, e.g., Kaposi's Sarcoma. AIDS is a major global health problem. The Joint United Nations Programme on HIV/AIDS (UNAIDS) estimates that there are now over 34 million people living with HIV or AIDS worldwide; some 28.1 million of those infected individuals reside in impoverished subSaharan Africa. In the United States, approximately one out of every 500 people are infected with HIV or have AIDS. Since the beginning of the epidemic, AIDS has killed nearly 19 million people worldwide, including some 425,000 Americans. AIDS has replaced malaria and tuberculosis as the world's deadliest infectious disease among adults and is the fourth leading cause of death worldwide. There remains a need for the identification of inhibitors of retroviral infection. To this end, there also remains a need for the development of methods for the identification of such inhibitors.

SUMMARY

Methods for identifying inhibitors of retroviral propagation, isolated tRNA fragments that are useful in these methods, and kits including these fragments, are disclosed. Also disclosed are methods of treating and/or preventing retroviral infection using the inhibitors of retroviral propagation, and pharmaceutical compositions including the inhibitors and a pharmaceutically-acceptable carrier. Combination therapy using one or more of the inhibitors, and a second anti-retroviral compound, are also disclosed.

The retroviral propagation can be inhibited by inhibiting retroviral reverse transcription, viral recruitment of the retroviral primer used in translation, human tRNA$^{Lys3}$, inhibiting the final packaging and assembly of new virions, and inhibiting the binding of a host cell tRNA to a target nucleic acid molecule.

Methods for screening inhibitors of retroviral propagation may involve forming a mixture comprising a linear sequence of a tRNA anticodon stem loop fragment, a nucleic acid molecule capable of binding to the tRNA anticodon stem loop fragment, and a test compound. The mixture is incubated under conditions that allow binding of the tRNA anticodon stem loop fragment and the nucleic acid molecule in the absence of the test compound. One can then determine whether or not a test compound inhibits the propagation of a retrovirus. Inhibition of binding of the tRNA ASL fragment and the target nucleic acid molecule is indicative of the test compound being an inhibitor of retroviral propagation.

In one aspect, the invention is directed to a method of identifying an inhibitor of retroviral reverse transcription. The method involves forming a mixture comprising a linear sequence of a tRNA anticodon stem loop fragment that is not capable of forming a stem-loop, a nucleic acid molecule capable of binding to the tRNA anticodon stem loop fragment, and a test compound. The mixture is incubated under conditions that allow the tRNA anticodon stem loop fragment and the nucleic acid molecule to bind in the absence of a test compound. One can then determine whether or not the test compound inhibits the binding of the tRNA anticodon stem loop fragment and the nucleic acid molecule. Binding of the tRNA ASL fragment and the target nucleic acid molecule is indicative of the test compound being an inhibitor of retroviral reverse transcription.

In yet another aspect, the invention is directed to a method of identifying an inhibitor of binding of a host cell tRNA and a target nucleic acid molecule. The method involves forming a mixture comprising a linear sequence of a tRNA anticodon stem loop fragment that is not capable of forming a stem-loop, a target nucleic acid molecule capable of binding to the tRNA anticodon stem loop fragment, and a test compound. The mixture is incubated under conditions that allow binding of the tRNA anticodon stem loop fragment and the target nucleic acid molecule in the absence of the test compound. One can then detect whether or not the test compound inhibits the binding of the tRNA fragment and the target nucleic acid molecule. Binding of the tRNA ASL fragment and the target nucleic acid molecule is indicative of the test compound being an inhibitor of retroviral reverse transcription, by inhibiting the RT complex from forming.

In another aspect, the invention is directed to a method of identifying an inhibitor of HIV recruitment of tRNA$^{Lys3}$ during translation of viral RNA to precursor proteins. The method involves forming a mixture comprising a linear sequence of a tRNA anticodon stem loop fragment that is not capable of forming a stem-loop, a target nucleic acid molecule capable of binding to the tRNA anticodon stem loop fragment, and a test compound, wherein the target nucleic acid molecule corresponds to a portion of a retroviral genome involved in HIV translation of viral RNA to precursor proteins. The mixture is incubated under conditions that allow binding of the tRNA anticodon stem loop fragment and the target nucleic acid molecule in the absence of the test compound. One can then detect whether or not the test compound inhibits the binding of the tRNA anticodon stem loop fragment and the target nucleic acid molecule. The absence of binding of the tRNA ASL fragment and the target nucleic acid molecule is indicative of the test compound being an inhibitor of retroviral translation.

In a further aspect, the invention is directed to a method of identifying an inhibitor of HIV final packaging & assembly of new virions, where one such example or embodiment would include tRNA$^{Lys3}$ being necessary for final viral packaging. The method involves forming a mixture comprising a linear sequence of a tRNA anticodon stem loop fragment that is not capable of forming a stem-loop, a target nucleic acid molecule capable of binding to the tRNA anticodon stem loop fragment, and a test compound, wherein the target nucleic acid molecule corresponds to a portion of a retroviral genome involved in final packaging and assembly. The mixture is incubated under conditions that allow binding of the tRNA anticodon stem loop fragment and the target nucleic acid molecule in the absence of the test compound. One can then detect whether or not the test compound inhibits the binding of the tRNA anticodon stem loop fragment and the target nucleic acid molecule. The absence of binding of the tRNA ASL fragment and the target nucleic acid molecule is indicative of the test compound being an inhibitor of retroviral final packaging & assembly of new virions by the inhibition of secondary virus spread through the decreasing of viral budding.

Kits for screening inhibitors of the various processes described above are also disclosed. The kits comprise a nucleic acid molecule consisting essentially of a linear sequence of a tRNA anticodon stem loop fragment; and a detectable label.

Compounds which are inhibitors of the various processes described above can be used in methods of treating and/or preventing viral infection, including retroviral infection. Such methods are also within the scope of the invention. Pharmaceutical compositions useful in these methods are also within the scope of the invention. Such pharmaceutical compositions include one or more inhibitors, as described herein, and a pharmaceutically-acceptable carrier. Combination therapy, using additional antiviral compounds which function by a different mechanism, are also disclosed.

DETAILED DESCRIPTION

Figure 1:
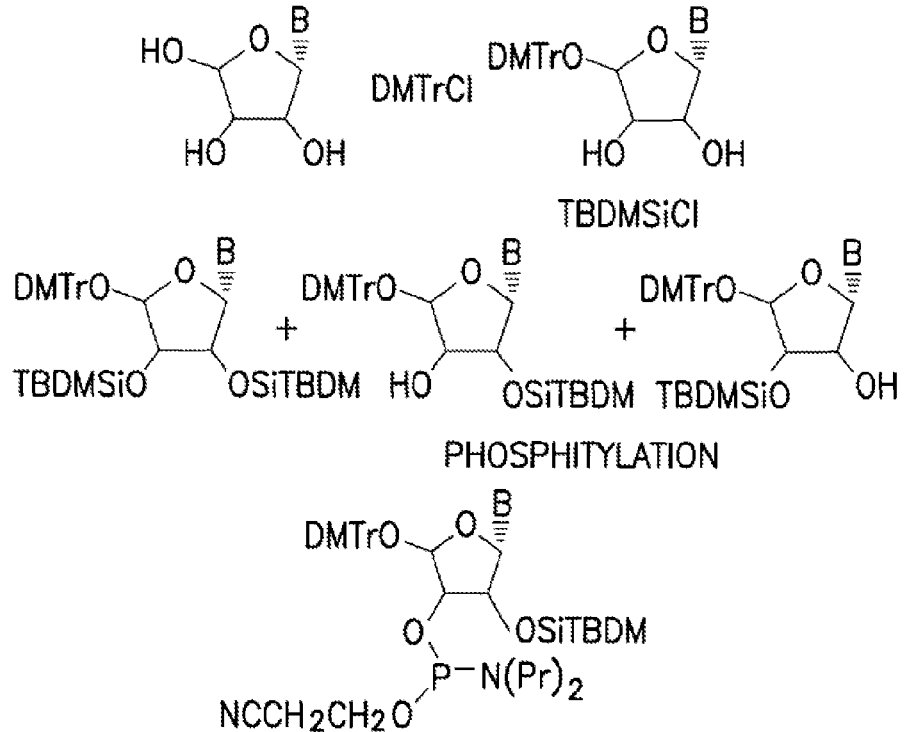
FIG. 1 provides a schematic representation of the protection of the modified nucleotides prior to synthesis of the RNA oligomer. Panel A illustrates protection with trifluoryl acetic acid. Panel B illustrates protection with benzoyl. Panel C illustrates the general protection of the ribose hydroxyl groups.
Figure 2:
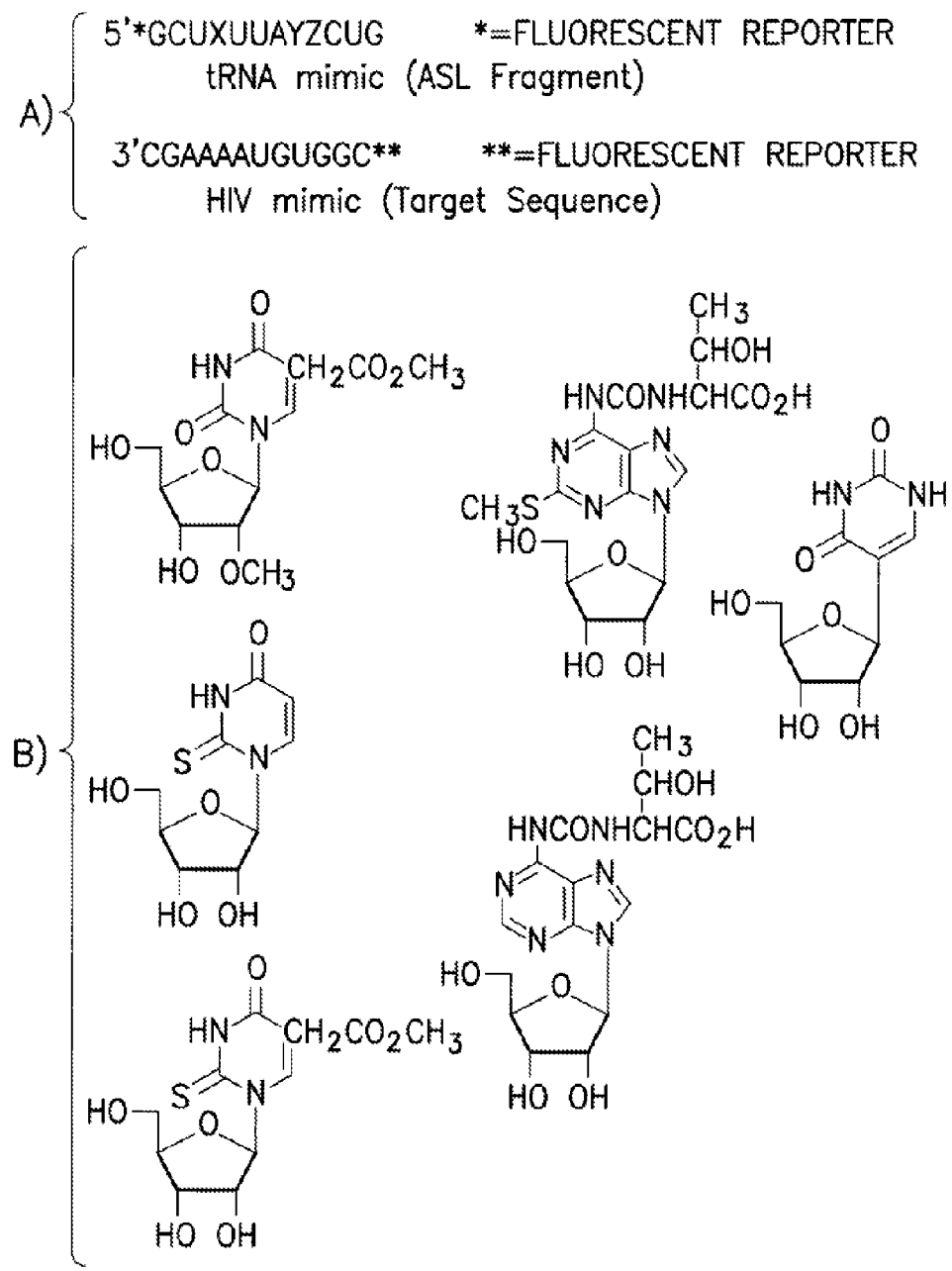
FIG. 2A provides a representation of a labeled tRNA fragment (SEQ ID NO: 2) and a corresponding target sequence (SEQ ID NO: 5).
FIG 2B provides structures of several representative modified nucleosides.

The present invention relates to compositions and methods for identifying compounds useful for inhibiting retroviral propagation, as well as pharmaceutical compositions and methods for treating viral infections by inhibiting retroviral propagation. Viral propagation can be inhibited by inhibiting reverse transcription, viral replication, translation of viral RNA into proteins, recruitment of human tRNA$^{Lys3}$, packaging and assembly of new virions, and/or inhibiting the binding of a host cell tRNA to a target nucleic acid molecule.

Prior to describing this invention in further detail, however, the following terms will first be defined.

Definitions:

As used herein, an "inhibitor" refers to any compound capable of preventing, reducing, or restricting retroviral propagation. An inhibitor may inhibit retroviral propagation, for example, by preventing, reducing or restricting retroviral reverse transcription. In some embodiments, the inhibition is at least 20% (e.g., at least 50%, 70%, 80%, 90%, 95%, 98%, 99%, 99.5%) of the retroviral propagation as compared to the propagation in the absence of the inhibitor. In one aspect, an inhibitor prevents, reduces, or restricts the binding of a tRNA, or fragment thereof, to a target nucleic acid molecule. Inhibitors can also affect recruitment of human tRNA$^{Lys3}$, translation of viral RNA into proteins, and/or final packaging and assembly of virions. Assays for analyzing inhibition are described herein and are known in the art.

An "RNA-dependent DNA polymerase" or "reverse transcriptase" is an enzyme that can synthesize a complementary DNA copy ("cDNA") from an RNA template. All known reverse transcriptases also have the ability to make a complementary DNA copy from a DNA template (target nucleic acid); thus, they are both RNA- and DNA-dependent DNA polymerases.

As used herein, a "label" or "detectable label" is any composition that is detectable, either directly or indirectly, for example, by spectroscopic, photochemical, biochemical, immunochemical, or chemical means. Useful labels include, but are not limited to, radioactive isotopes (for example, 32p, 35S, and 3H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. Moreover, a label or detectable moiety can include an "affinity tag" that, when coupled with the target nucleic acid and incubated with a test compound or compound library, allows for the affinity capture of the target nucleic acid along with molecules bound to the target nucleic acid. One skilled in the art will appreciate that an affinity tag bound to the target nucleic acid has, by definition, a complimentary ligand coupled to a solid support that allows for its capture. For example, useful affinity tags and complimentary partners include, but are not limited to, biotin-streptavidin, complimentary nucleic acid fragments (for example, oligo dT-oligo dA, oligo T-oligo A, oligo dG-oligo dC, oligo G-oligo C), aptamers, or haptens and proteins for which antisera or monoclonal antibodies are available. The label or detectable moiety is typically bound, either covalently, through a linker or chemical bound, or through ionic, van der Waals or hydrogen bonds to the molecule to be detected.

I. Methods for Identifying an Inhibitor of Retroviral Propogation

Inhibitors of viral propagation, for example, retroviral propagation, can be identified using the methods described herein. The retroviral propagation can be inhibited, for example, by a) inhibiting retroviral reverse transcription, b) inhibiting the binding of a host cell tRNA and a target nucleic acid molecule, c) inhibiting the viruses recruitment of the retroviral primer, human tRNA$^{Lys3}$, d) inhibiting HIV translation of viral RNA to precursor proteins, and/or e) inhibiting HIV's final packaging and assembly.

These individual methods for identifying inhibitors of retroviral propagation are discussed below.

Identifying Inhibitors of Retroviral Reverse Transcription

In one aspect, the method can be used to identify inhibitors of retroviral reverse transcription. In another aspect, the methods can be used to identify inhibitors of tRNA binding to a target nucleic acid molecule. In another aspect, the methods can be readily adapted for use in high through-put assays. Transfer RNA (tRNA) is involved in reverse transcription through the recognition of a corresponding site on the retroviral genome priming reverse transcription. Identifying inhibitors of reverse transcription may lead to the identification of therapeutic compounds for use in treating retroviral infection in a host cell.

The method comprises forming a mixture having a tRNA anticodon stem-loop (ASL) fragment, a target nucleic acid molecule that is capable of binding to the tRNA fragment, and a test compound. In one aspect, the target nucleic acid molecule corresponds to a fragment of the retroviral genome involved in reverse transcription. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where the absence of binding of the tRNA ASL fragment and the target nucleic acid molecule is indicative of the test compound being an inhibitor of retroviral reverse transcription. In one aspect, the detection involves the use of labels to detect the inhibition of binding of the tRNA fragment to the target nucleic acid molecule.

Methods for Identifying Inhibitors of Binding of a Host Cell tRNA to a Target Nucleic Acid Molecule In another aspect, the method can also be used to identify an inhibitor of binding of a tRNA to a target nucleic acid molecule. The method comprises forming a mixture containing a host cell tRNA ASL fragment, a target nucleic acid molecule that is capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid, where binding of the tRNA ASL fragment and the target nucleic acid molecule is indicative of the test compound being an inhibitor of binding of a tRNA to a target nucleic acid molecule. In one aspect, the detection involves the use of labels to detect the inhibition of binding of the tRNA fragment to the target nucleic acid molecule.

Methods for Identifying Inhibitors of HIV Reverse Transcription (RT) Complex Formation In another aspect, the method can be used to identify an inhibitor of HIV reverse transcriptase (RT) complex formation. The method involves forming a mixture containing a tRNA ASL fragment, a target nucleic acid molecule capable of binding to the tRNA fragment, and a test compound. The resulting mixture is incubated under conditions that allow binding of the tRNA fragment and the target nucleic acid in the absence of the test compound. The method further involves detecting whether the test compound inhibits the binding of the tRNA fragment to the target nucleic acid. In one aspect, the detection involves the use of labels to detect the inhibition of binding of the tRNA fragment to the target nucleic acid molecule, where the inhibition indicates that the test compound is capable of inhibiting the formation of the RT complex.

In another aspect, the methods may involve the detection of the binding of the test compound to either the tRNA fragment, the target nucleic acid, or both the tRNA fragment and the target nucleic acid. In one aspect, the binding of the test compound is indicative of the test compound being an inhibitor of retroviral propagation, retroviral infection, reverse transcription, or tRNA binding.

Methods for Identifying Inhibitors of Viral Recruitment of Human tRNA$^{Lys3}$.

In yet another aspect, the method can be used to identify an inhibitor of HIV's recruitment of the retroviral primer, human tRNA$^{Lys3}$. The method involves forming a mixture comprising a linear sequence of a tRNA anticodon stem loop fragment that is not capable of forming a stem-loop, a target nucleic acid molecule capable of binding to the tRNA anticodon stem loop fragment, and a test compound, wherein the target nucleic acid molecule corresponds to a portion of a retroviral genome involved in recruitment of retroviral primer recruitment. The mixture is incubated under conditions that allow binding of the tRNA anticodon stem loop fragment and the target nucleic acid molecule in the absence of the test compound. One can then detect whether or not the test compound inhibits the binding of the tRNA anticodon stem loop fragment and the target nucleic acid molecule. The absence of binding of the tRNA ASL fragment and the target nucleic acid molecule is indicative of the test compound being an inhibitor retroviral primer recruitment.

Methods for Identifying Inhibitors of Viral RNA Translation

In still another aspect, a method of identifying an inhibitor of viral RNA translation to viral precursor proteins is provided. The method involves forming a mixture comprising a linear sequence of a tRNA anticodon stem loop fragment that is not capable of forming a stem-loop, a target nucleic acid molecule capable of binding to the tRNA anticodon stem loop fragment, and a test compound; incubating the mixture under conditions that allow binding of the tRNA anticodon stem loop fragment and the target nucleic acid molecule in the absence of the test compound; and detecting whether or not the test compound inhibits the binding of the tRNA fragment and the target nucleic acid molecule where binding of the tRNA ASL fragment and the target nucleic acid molecule is indicative of the test compound being an inhibitor of tRNA recruitment during viral RNA translation to viral precursor proteins.

The inhibitors identified by any of the methods disclosed herein can inhibit the retroviral infection by inhibiting any step of a virus lifecycle, including, but not limited to, reverse transcription, viral assembly, RT complex formation, recruitment of the retroviral primer, human tRNA$^{Lys3}$, translation of viral RNA to precursor proteins, and the final packaging and assembly. Moreover, the inhibitors identified may inhibit retroviral infection, delay the infection, or slow the progression of the infection. Accordingly, methods of treatment using the inhibitors are also intended to be within the scope of the invention.

II. Retroviruses Whose Propagation can be Inhibited

Retroviruses for which inhibitors can be identified by the methods disclosed herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), mutated versions thereof, and the like.

Inhibitors of HIV are also active against the hepatitis B virus (HBV), and can be used in methods of treating and/or preventing HBV infection, and pharmaceutical compositions intended for this use.

III. tRNA Fragments Useful in the Methods Described Herein

The tRNA fragments (or "tool tRNA fragments") for use in the screening methods described herein can be a fragment from any tRNA. Specific tRNA fragments described in the formulas below are another aspect of the invention, and these fragments can be included in the kits described herein.

The tRNA fragments (or "tool tRNA fragments") for use in the methods of the present disclosure can be a fragment from any tRNA. The tRNA fragment may be obtained or derived from or corresponds to a $tRNA^{Ala}$, $tRNA^{Arg}$, $tRNA^{Asn}$, $tRNA^{Asp}$, $tRNA^{Cys}$, $tRNA^{Gln}$, $tRNA^{Glu}$, $tRNA^{Gly}$, $tRNA^{His}$, $tRNA^{Ile}$, $tRNA^{Leu}$, $tRNA^{Lys}$, $tRNA^{Met}$, $tRNA^{Phe}$, $tRNA^{Pro}$, $tRNA^{Ser}$, $tRNA^{Thr}$, $tRNA^{Trp}$, $tRNA^{Tyr}$, and $tRNA^{Val}$. In one aspect, the tRNA fragment corresponds to $tRNA^{Lys}$. In another aspect, the tRNA fragment is derived from or corresponds to the $tRNA^{Lys}$ anticodon stem loop (ASL). In another aspect, the tRNA fragment corresponds to a fragment of nucleotides 32-43 of the human $tRNA^{Lys}$. The position numbers used herein refer to the nucleotide position numbering of the conventional tRNA numbering as disclosed in Sprinzl, et al. *Nucl. Acids. Res.*, 26, 148-153 (1998). In one aspect, the tRNA fragment is a fragment from a host cell tRNA, such as a mammalian host cell, including, but not limited to, human, feline, and simian host cells.

The tRNA fragments may incorporate one or more modified nucleosides. In one aspect, the tRNA fragment incorporates one, two, three, or more modified nucleosides into the nucleic acid sequence. In another aspect, the tRNA fragments incorporate three modified nucleosides into the tRNA fragment nucleic acid molecules. Modified nucleosides that can be incorporated into the tRNA fragments include any modified nucleotide, including, but not limited to 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5Cm), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2,2'$-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), 5-methylaminomethyluridine (mnm5U), 2-thiouridine (s2U), 2'-O-methyluridine (Um), 4-thiouridine (s4U), 5-carbamoylmethyluridine (ncm5U), 5-methoxycarbonylmethyluridine (mcm5U), 5-methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5-carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (Ψ), 1-methylpseudouridine (m1Ψ), 2'-O-methylpseudouridine (Ψm), ribosylthymine (m5U), 5-methyl-2-thiouridine (m5s2U), and 5,2'-O-dimethyluridine (m5Um).

In a preferred aspect, the fragment tRNA contains modified nucleic acids Corresponding to positions 34, 37, and 39 in the anticodon stem loop of a tRNA. The position numbers used herein refer to the nucleotide position numbering of the conventional tRNA numbering as disclosed in Sprinzl, et al. *Nucl. Acids. Res.*, 26, 148-153 (1998). In one aspect, the tRNA fragment comprises, or consists of, a molecule having the sequence 5'-GCUXUUAYZCUG (SEQ ID NO: 1), in which the X, Y, and Z refer to modified or unmodified nucleosides. In one aspect, the X, Y, and Z refer to modified nucleosides, such as mnm5s2U, mcm5s2U, ms2t6A, s2U, ψ, and t6A. In another aspect, the tRNA fragment has the nucleic acid sequence 5'-CU(mnm5s2U)UU(ms2t6A)A(ψ)CUGC (SEQ ID NO: 2). In another aspect, the tRNA fragment has the nucleic acid sequence 5'-GCU(mnm5s2U)UU(ms2t6A)A(ψ)CUG (SEQ Id NO: 3).

The tRNA fragment may correspond to any portion of the tRNA involved in propagation of the retrovirus through binding, directly or indirectly, to the retroviral genome. In a preferred aspect, the tRNA fragment corresponds to the anticodon stem loop (ASL) of the tRNA.

The tRNA fragment may correspond to any portion of the host cell's tRNA involved in nucleotide binding, such as involvement in the reverse transcription (RT) complex formation. For example, the tRNA may be involved in binding to a retroviral genome to initiate, prime, or facilitate reverse transcription of the retroviral genome. In one aspect, the fragment tRNA corresponds to a fragment of the anticodon stem loop of any tRNA. In one aspect, the fragment corresponds to a fragment from the anticodon stem loop of $tRNA^{-Lys}$. In another aspect, the tRNA fragment corresponds to a fragment from the anticodon stem loop of human $tRNA^{-Lys}$. In another aspect, the tRNA fragment corresponds to a fragment from nucleotides 32-43 of human $tRNA^{Lys3}$.

The tRNA fragment may also be any length of a fragment from a tRNA. In one aspect, the tRNA fragment comprises a fragment of between 9 to 15 continuous nucleotides of a tRNA, 10 to 14 continuous nucleotides of a tRNA, or between 11 to 13 continuous nucleotides of a tRNA. In another aspect, the fragment is a fragment of 8, 9, 10, 11, 12, 13, 14, 15, or 16 continuous nucleotides of a tRNA. In a further aspect, the fragment is a fragment of 12 continuous nucleotides of a tRNA.

The tRNA fragment may or may not be capable of forming a secondary structure. In a one aspect, the tRNA fragment is not capable of forming a stem loop structure with itself. In another aspect, the fragment is a linear fragment of a tRNA that is not capable of forming a stem loop structure with itself.

The tRNA fragment may also be linked to additional nucleic acids. For example, the tRNA fragment may be linked to one or more additional nucleic acids depending on the assay method. In one aspect, the tRNA fragment may be linked to nucleotides used to attach the fragment to a solid support surface. In another aspect, the fragment tRNA is linked to additional nucleic acid molecules at one or both terminal end of the tRNA fragment. In another aspect, the fragment tRNA is linked to additional nucleic acid molecules at both terminal ends. The additional nucleic acid sequences can be any length, preferably between 8 and 16 nucleotides, between 10 and 14 nucleotides, more preferably 12 nucleotides in length. In one aspect, the terminal sequences do not allow the tRNA fragment to form a secondary structure, such as a hairpin loop structure.

A target nucleic acid molecule may correspond to any nucleic acid molecule, such as a DNA or an RNA molecule that is involved in retroviral propagation or retroviral reverse transcription. In one aspect, the target nucleic acid molecule corresponds to any nucleic acid molecule that is capable of binding to the tRNA fragment and is involved in retroviral propagation or reverse transcription. In another aspect, the target nucleic acid molecule corresponds to a nucleic acid molecule involved in reverse transcription of a retroviral genome. In another aspect, the target nucleic acid molecule corresponds to ribonucleic acid from a retroviral genome. In another aspect, the target nucleic acid molecule corresponds to a nucleic acid molecule that is involved in priming retroviral reverse transcription.

The target nucleic acid molecule may be any length and may include the entire retroviral genome and fragments thereof. In one aspect, the target nucleic acid molecule includes any fragment of a retroviral genome involved in tRNA binding, and includes fragments of at least 5, 6, 7, 8, 9, 10, 11, 12, 13, 14, 15, 20, 25, 30, 35, 40, 45, 50 or more nucleotides. In another aspect, the target nucleic acid is about the same, or is the same length as the tool tRNA fragment.

In another aspect, the target nucleic acid molecule corresponds to a nucleic acid molecule from a Human Immunodeficiency Virus (HIV), such as HIV-1 or HIV-2. In another aspect, the target molecule corresponds to HIV-1. In another aspect, the target nucleic acid molecule corresponds to a nucleic acid molecule involved in priming HIV reverse transcription.

Such target nucleic acid molecules can be derived from or correspond to any portion of the HIV genome involved in reverse transcription through the binding or association with a host cell tRNA. In one aspect, the target nucleic acid molecule is derived from or corresponds to the 5' untranslated region of the HIV genome. In another aspect, the target nucleic acid molecule corresponds to a fragment including residues 157 to 169 of the 5' untranslated region of HIV-1. The target nucleic acid sequence may be complementary to the tRNA fragment. In a one aspect, the target nucleic acid molecule comprises the nucleic acid sequence 5'-GCGGU-GUAAAAG (SEQ ID NO: 4).

Specific Isolated tRNA Fragments

In one aspect, the isolate tRNA fragment comprises the sequence 5'-GCUXUUAYZCUG (SEQ ID NO: 1), in which the X, Y, and Z refer to modified nucleosides.

Representative modified nucleosides include 1-methyladenosine (m1A), 2-methyladenosine (m2A), $N^6$-isopentenyladenosine (i6A), 2-methylthio-$N^6$-isopentenyladenosine (ms2i6A), $N^6$-methyladenosine (m6A), $N^6$-threonylcarbamoyladenosine (t6A), $N^6$-methyl-$N^6$ threonylcarbomoyladenosine (m6t6A), 2-methylthio-$N^6$-threonylcarbamoyladenosine (ms2t6A), 2'-O-methyladenosine I Inosine (Am), 1-methylinosine Ar(p) 2'-O-(5-phospho)ribosyladenosine (m1I), $N^6$-(cis-hydroxyisopentenyl)adenosine (io6A), 2-thiocytidine (s2C), 2'-O-methylcytidine (Cm), $N^4$-acetylcytidine (ac4C), 5-methylcytidine (m5C), 3-methylcytidine (m3C), lysidine (k2C), 5-formylcytidin (f5C), 2'-O-methyl-5-formylcytidin (f5Cm), 2'-O-(5phospho) ribosylguanosine (Gr(p)), 1-methylguanosine (m1G), $N^2$-methylguanosine (m2G), 2'-O-methylguanosine (Gm), $N^2N^2$-dimethylguanosine (m22G), $N^2,N^2,2$'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (02yW), 5-methylaminomethyluridine (mnm5U), 2-thiouridine (s2U), 2'-O-methyluridine (Um), 4-thiouridine (s4U), 5-carbamoylmethyluridine (ncm5U), 5-methoxycarbonylmethyluridine (mcm5U), 5-methylaminomethyl-2-thiouridine (mnm5s2U), 5-methoxycarbonylmethyl-2-thiouridine (mcm5s2U), uridine 5-oxyacetic acid (cmo5U), 5-methoxyuridine (mo5U), 5-carboxymethylaminomethyluridine (cmnm5U), 5-carboxymethylaminomethyl-2-thiouridine (cmnm5s2U), 3-(3-amino-3-carboxypropyl)uridine (acp3U), 5-(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (Ψ), 1-methylpseudouridine (m1Ψ), 2'-O-methylpseudouridine (Ψm), ribosylthymine (m5U), 5-methyl-2-thiouridine (m5s2U), and 5,2'-O-dimethyluridine (m5Um).

In one embodiment, the modified nucleosides are mnm5s2U, mcm5s2U, ms2t6A, s2U, ψ, or t6A.

One specific tRNA fragment comprises the nucleic acid sequence 5'-CU(mnm5s2U)UU(ms2t6A)A(ψ)CUGC (SEQ ID NO: 2).

Another specific tRNA fragment comprises the nucleic acid sequence 5'-GCU(mnm5s2U)UU(ms2t6A)A(ψ)CUG (SEQ ID NO: 3).

Any of these tRNA fragments can further comprise a label. The label can be detectable, either directly or indirectly, by spectroscopic, photochemical, biochemical, immunochemical, or chemical means.

Representative labels include radioactive isotopes (for example, $^{32}$P, $^{35}$S, and $^3$H), dyes, fluorescent dyes (for example, Cy5 and Cy3), fluorophores (for example, fluorescein), electron-dense reagents, enzymes and their substrates (for example, as commonly used in enzyme-linked immunoassays, such as, alkaline phosphatase and horse radish peroxidase), biotin-streptavidin, digoxigenin, or hapten; and proteins for which antisera or monoclonal antibodies are available. The label can also be an "affinity tag."

Where the label comprises an affinity tag, the isolated tRNA fragments can be captured with a complimentary ligand coupled to a solid support that allows for the capture of the affinity tag-labeled tRNA fragment. Representative affinity tags and complimentary partners include biotin-streptavidin, complimentary nucleic acid fragments (for example, oligo dT-oligo dA, oligo T-oligo A, oligo dO-oligo dC, oligo O-oligo C), aptamers, or haptens and proteins for which antisera or monoclonal antibodies are available.

When a biological interaction brings the beads together, a cascade of chemical reactions acts to produce a greatly amplified signal. On laser excitation, a photosensitizer in the "Donor" bead converts ambient oxygen to a more excited singlet state. The singlet state oxygen molecules diffuse across to react with a thioxene derivative in the Acceptor bead generating chemiluminescence at 370 nm that further activates fluorophores contained in the same bead. The fluorophores subsequently emit light at 520-620 nm.

In one example of a commercially-available alpha bead, the Donor beads comprise biotin or are directly bound to RNA. The Acceptor beads include a His6 tag, hemagglutinin (HA), digoxin/digoxigenin (DIG), or fluorescein (FITC).

IV. Synthetic Methods for Producing Isolated Ribonucleotides

A variety of methods are known in the art for making nucleic acids having a particular sequence or that contain particular nucleic acid bases, sugars, internucleoside linkages, chemical moieties, and other compositions and characteristics. Anyone or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach 2nd ed., Cold Spring Harbor Laboratory Press, 1989) such as, but not limited to a plasmid, bacteriophage (e.g., mB or lamda), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with non-naturally-occurring bases, sugars, and internucleoside linkages are commercially available (e.g., see the 2000 Product and Service Catalog, TriLink Biotechnologies, San Diego, Calif., USA)

The tRNA fragment or the target nucleic acid, or both the tRNA fragment and the target nucleic acid molecule may be detectably labeled to facilitate detection. In a preferred aspect, the tRNA fragment is labeled with a fluorophore to facilitate detection. In another aspect, the target nucleic acid molecule is labeled with biotin to facilitate detection. In another preferred aspect, the tRNA fragment is labeled with a fluorophore and the target nucleic acid molecule is labeled with biotin.

The tRNA fragment and target nucleic acid molecule may be labeled, for example, at either the 5' terminus, the 3'-terminus, or combinations of the 5'-terminus and the 3' terminus to facilitate detection. In addition, the test compound may also be labeled. In another embodiment, the tRNA fragment and the target nucleic acid molecule may have a detectable label attached to an internal position of the molecule to facilitate detection.

V. Methods for Detecting Binding (or Inhibition Thereof) of Target RNA to tRNA

The methods for detecting binding of the target RNA to the tRNA or the inhibition of such binding may be performed using any method for such detection. For example, the AlphaScreen® assay (Packard Instrument Company, Meriden, Conn.). AlphaScreen® technology is an "Amplified Luminescent Proximity Homogeneous Assay" method utilizing latex microbeads (250 nm diameter) containing a photosensitizer (donor beads), or chemiluminescent groups and fluorescent acceptor molecules (acceptor beads). Upon illumination with laser light at 680 nm, the photosensitizer in the donor bead converts ambient oxygen to singlet-state oxygen. The excited singlet-state oxygen molecules diffuse approximately 250 nm (one bead diameter) before rapidly decaying. If the acceptor bead is in close proximity to the donor bead (i.e., by virtue of the interaction of the target RNA and tRNA fragment), the singlet-state oxygen molecules reacts with chemiluminescent groups in the acceptor beads, which immediately transfer energy to fluorescent acceptors in the same bead. These fluorescent acceptors shift the emission wavelength to 520-620 nm, resulting in a detectable signal. Antagonists of the interaction of the target RNA with the tRNA fragment will thus inhibit the shift in emission wavelength, whereas agonists of this interaction would enhance it.

The disclosed methods may be performed by mixing the component nucleotide (e.g. the tool tRNA and the target RNA) and the test compound in any order, or simultaneously. For example, a target RNA may be first combined with a test compound to form a first mixture, and then a tool tRNA fragment may be added to form a second mixture. In another example, a target RNA, a tool tRNA and the test compound may all be mixed at the same time before incubation. In one aspect, the mixture is incubated under conditions that allow binding of the tRNA fragment and the target nucleic acid in the absence of the test compound.

The inhibition of binding of the tRNA fragment and the target nucleic acid molecule by the test compound may be detected using any method available for the detection of inhibition. In one aspect, the determining step may be performed using methods including, but not limited to, gel shift assays, chemical and enzymatic footprinting, circular dichroism and NMR spectroscopy, equilibrium dialysis, or in any of the binding detection mechanisms commonly employed with combinatorial libraries of probes or test compounds. The inhibition of binding indicates that the test compound may be useful for inhibiting propagation of the virus in the host.

VI. Evaluating Compounds for their Ability to Inhibit Binding

Any compound may be tested using the methods described herein to identify compounds capable of inhibiting retroviral propagation. Test compounds that may be screened with methods of the present invention include, but are not limited to, polypeptides, beta-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, structural analogs or combinations thereof. Some test compounds are synthetic molecules while others are natural molecules.

Test compounds may be obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

In another aspect, the test compounds may be naturally occurring proteins or their fragments. Such test compounds may be obtained from a natural source, e.g., a cell or tissue lysate. Libraries of polypeptide agents may also be prepared, e.g., from a cDNA library commercially available or generated with routine methods. The test compounds can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides. In some methods, the test compounds are polypeptides or proteins.

In another aspect, the test compounds may be nucleic acids. Nucleic acid test compounds may be naturally occurring nucleic acids, random nucleic acids, or "biased" random nucleic acids. For example, digests of prokaryotic or eukaryotic genomes may be similarly used as described above for proteins.

In some preferred methods, the test compounds are small molecules, e.g., molecules with a molecular weight of not more than about 500 or 1,000. Preferably, high throughput assays are adapted and used to screen for such small molecules. In some methods, combinatorial libraries of small molecule test compounds as described above can be readily employed to screen for small molecule modulators of retroviral propagation. A number of assays are available for such screening, e.g., as described in Schultz et al., Bioorg Med Chem Lett 8:2409-2414, 1998; Weller et al., Mol Divers. 3:61-70, 1997; Fernandes et al., Curr Opin Chem Biol 2:597-603, 1998; and Sittampalam et al., Curr Opin Chem Biol 1:384-91, 1997.

The methods of the present invention may further be adapted for use in high through-put assays for screening for inhibitors of retroviral propagation, such as reverse transcriptase inhibitors. Such high through-put (HTS) assays may involve attaching or binding either the tRNA fragment or the target nucleic acid molecule to a solid support. A "solid support" may be any surface to which molecules may be attached through either covalent or non-covalent bonds. This includes, but is not limited to, membranes, plastics, magnetic beads, charged paper, nylon, Langmuir-Bodgett films, functionalized glass, germanium, silicon, PTFE, polystyrene, gallium arsenide, gold, and silver. Any other material known in the art that is capable of having functional groups such as amino, carboxyl, thiol or hydroxyl incorporated on its surface, is also contemplated. This includes surfaces with any topology, including, but not limited to, spherical surfaces and grooved surfaces. HTS methods generally refer to technologies that permit the rapid assaying of test compounds for therapeutic potential, for example, by inhibiting the binding of a tRNA fragment to a target nucleic acid molecule. HTS techniques employ robotic handling of test materials, detection of positive signals, and interpretation of data. Test compounds may be identified via the detection of luminescence or absence of luminescence through the use of radioactivity or through optical assays that rely on absorbance, fluorescence or luminescence as read-outs. Gonzalez, J. E. et al., (1998) Curro Opin. Biotech. 9:624-631.

The invention also comprises kits and compositions (e.g., reaction mixtures, etc.) for a method of the invention. A kit is a combination of individual compositions useful or sufficient for carrying out one or more steps a method of the invention, wherein the compositions are optimized for use together in the method. A composition comprises an individual component for at least one step of a method of the invention. The present invention further provides a kit for screening for an inhibitor of retroviral reverse transcription, comprising: a linear sequence of a tRNA anticodon stem loop fragment and a reagent for detection of binding to a target sequence, such as a label. In some embodiments, the kit also comprises one or more target nucleic acid molecule(s) that are capable of binding to the tRNA anticodon stem loop fragment. In some embodiments, the kit further comprises additional reagents for conducting the screening methods. In some embodiments, the kit further comprises a plurality of inhibitors of retroviral reverse transcription. In some embodiments, the reagent comprises a dye that undergoes fluorescence enhancement upon binding to nucleic acids (e.g., the dye is RIBOGREEN, SYBR Gold, SYBR Green I, or SYBER Green II). In some embodiments, the kit further comprises control reagents (e.g., sample polymerases and/or inhibitors for positive controls, polymerase and/or inhibitor minus samples for negative controls, etc.). In some embodiments, the kit further comprises instructions for carryout out the methods. In some embodiments, the instructions are embodied in computer software that assists the user in obtaining, analyzing, displaying, and/or storing results of the method. The software may further comprise instructions for managing sample information, integrating with scientific equipment (e.g., detection equipment), etc.

VII. Kits for Identifying Inhibitors

Also provided are kits for identifying inhibitors for the various processes described herein, namely, inhibitors of retroviral propagation, retroviral reverse transcription, binding to host cell tRNA and a target nucleic acid molecule, viral RNA translation, and final viral packaging and assembly.

In one aspect, the kits include a tRNA fragment as described herein and a nucleic acid molecule capable of binding to the tRNA fragment. The kits of the present invention may also include target nucleic acid sequences, and/or reagents for performing the assays. The kits may also include labeling components for detecting whether a test compound inhibits the binding of the fragment tRNA and the nucleic acid molecule.

VIII. Methods of Treatment

As disclosed herein, for example, in the working examples below, several compounds have been identified that are capable of inhibiting viral propagation. The retroviral propagation can be inhibited by inhibiting retroviral reverse transcription, viral recruitment of the retroviral primer used in translation, human tRNA$^{Lys3}$, inhibiting the final packaging and assembly of new virions, and/or inhibiting the binding of a host cell tRNA to a target nucleic acid molecule.

Accordingly, these compounds can be used in methods to treat patients suffering from retroviral infections. That is, a retroviral viral infection can be treated or prevented by administering one or more inhibitors of retroviral propagation, for example, inhibitors of retroviral reverse transcription, binding to host cell tRNA and a target nucleic acid molecule, recruitment of the retroviral primer, human tRNA$^{Lys3}$, viral RNA translation into viral proteins, and final viral packaging and assembly of virions. Treatment of viral disease has not been heretofore accomplished by using such inhibitors.

The compounds can be used to treat or prevent viral infections, including infections by retroviruses, and/or to inhibit viral replication, propagation, reverse transcription, mRNA translation, and/or final viral packaging and assembly. Retroviruses for which inhibitors can be identified by the methods disclosed herein include any viruses having RNA as their primary genetic material and use reverse transcription to produce DNA. Such viruses include, but are not limited to, Feline Immunodeficiency Virus (FIV), Simian Immunodeficiency Virus (SIV), Avian Leucosis Virus, Feline Leukemia Virus, Walleye Dermal Sarcoma Virus, Human T-Lymphotropic Virus, and Human Immunodeficiency Viruses (HIV). In a preferred aspect, the retrovirus is HIV. HIV can be any strain, form, subtype or variation in the HIV family. HIV viruses include, but are not limited to, HIV-I, HIV-II, HIV-III (also known as HTLV-II, LAV-I, LAV-2), and the like.

The compounds can also be used as adjunct therapy in combination with existing therapies in the management of the aforementioned types of viral infections. In such situations, it is preferably to administer the active ingredients to a patient in a manner that optimizes effects upon viruses, including mutated, multi-drug resistant viruses, while minimizing effects upon normal cell types. While this is primarily accomplished by virtue of the behavior of the compounds themselves, this can also be accomplished by targeted drug delivery and/or by adjusting the dosage such that a desired effect is obtained without meeting the threshold dosage required to achieve significant side effects.

IX. Pharmaceutical Compositions

The inhibitory compounds as described herein can be incorporated into pharmaceutical compositions and used to treat or prevent a viral infection, such as a retroviral infection. The pharmaceutical compositions described herein include the inhibitory compounds as described herein, and a pharmaceutically acceptable carrier and/or excipient.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions may be formulated in unit dose form, or in multiple or subunit doses. Preferred compositions are in liquid or semisolid form. Compositions including a liquid pharmaceutically inert carrier such as water or other pharmaceutically compatible liquids or semisolids may be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is a preferred method of injection. Suitable carriers for injection are well known to those of skill in the art, and include 5% dextrose solutions, saline, and phosphate buffered saline. The compounds can also be administered as an infusion or injection (e.g., as a suspension or as an emulsion in a pharmaceutically acceptable liquid or mixture of liquids).

The formulations may also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations may depend on the particular composition used and the particular subject receiving the treatment. These formulations may contain a liquid carrier that may be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, the compositions are administered such that active ingredients interact with regions where viral infections are located. The compounds described herein are very potent at treating these viral infections.

In certain circumstances, the compounds described herein can be employed as part of a pharmaceutical composition with other compounds intended to prevent or treat a particular viral infection, i.e., combination therapy. In addition to effective amounts of the compounds described herein, the pharmaceutical compositions can also include various other components as additives or adjuncts.

Combination Therapy

Combination therapy may be administered as (a) a single pharmaceutical composition which comprises an inhibitory compound as described herein, at least one additional pharmaceutical agent described herein, and a pharmaceutically acceptable excipient, diluent, or carrier; or (b) two separate pharmaceutical compositions comprising (i) a first composition comprising an inhibitory compound as described herein and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions can be administered simultaneously or sequentially and in any order.

In use in treating or preventing viral disease, the inhibitory compound(s) can be administered together with at least one other antiviral agent as part of a unitary pharmaceutical composition. Alternatively, it can be administered apart from the other antiviral agents. In this embodiment, the inhibitory compound and the at least one other antiviral agent are administered substantially simultaneously, i.e. the compounds are administered at the same time or one after the other, so long as the compounds reach therapeutic levels for a period of time in the blood.

Combination therapy involves administering the inhibitory compound, as described herein, or a pharmaceutically acceptable salt or prodrug of the inhibitory compound, in combination with at least one anti-viral agent, ideally one which functions by a different mechanism than the inhibitors of viral propagation described herein.

Representative Antiviral Agents

Some antiviral agents which can be used for combination therapy include agents that interfere with the ability of a virus to infiltrate a target cell. The virus must go through a sequence of steps to do this, beginning with binding to a specific "receptor" molecule on the surface of the host cell and ending with the virus "uncoating" inside the cell and releasing its contents. Viruses that have a lipid envelope must also fuse their envelope with the target cell, or with a vesicle that transports them into the cell, before they can uncoat.

There are two types of active agents which inhibit this stage of viral replication. One type includes agents which mimic the virus-associated protein (VAP) and bind to the cellular receptors, including VAP anti-idiotypic antibodies, natural ligands of the receptor and anti-receptor antibodies, receptor anti-idiotypic antibodies, extraneous receptor and synthetic receptor mimics. The other type includes agents which inhibit viral entry, for example, when the virus attaches to and enters the host cell. For example, a number of "entry-inhibiting" or "entry-blocking" drugs are being developed to fight HIV, which targets the immune system white blood cells known as "helper T cells", and identifies these target cells through T-cell surface receptors designated "CRX4" and "CCR5". Thus, CRX4 and CCR5 receptor inhibitors such as amantadine and rimantadine, can be used to inhibit viral infection, such as HIV, influenza, and hepatitis B and C viral infections. Another entry-blocker is pleconaril, which works against rhinoviruses, which cause the common cold, by blocking a pocket on the surface of the virus that controls the uncoating process.

Further antiviral agents that can be used in combination with the inhibitory compounds described herein include agents which interfere with viral processes that synthesize virus components after a virus invades a cell. Representative agents include nucleotide and nucleoside analogues that look like the building blocks of RNA or DNA, but deactivate the enzymes that synthesize the RNA or DNA once the analogue is incorporated. Acyclovir is a nucleoside analogue, and is effective against herpes virus infections. Zidovudine (AZT), 3TC, FTC, and other nucleoside reverse transcriptase inhibitors (NRTI), as well as non-nucleoside reverse transcriptase inhibitors (NNRTI), can also be used. Integrase inhibitors can also be used.

Once a virus genome becomes operational in a host cell, it then generates messenger RNA (mRNA) molecules that direct the synthesis of viral proteins. Production of mRNA is initiated by proteins known as transcription factors, and certain active agents block attachment of transcription factors to viral DNA.

Other active agents include antisense oligonucleotides and ribozymes (enzymes which cut apart viral RNA or DNA at selected sites).

Some viruses, such as HIV, include protease enzymes, which cut viral protein chains apart so they can be assembled into their final configuration. Protease inhibitors are another type of antiviral agent that can be used in combination with the inhibitory compounds described herein.

The final stage in the life cycle of a virus is the release of completed viruses from the host cell. Some active agents, such as zanamivir (Relenza) and oseltamivir (Tamiflu) treat influenza by preventing the release of viral particles by blocking a molecule named neuraminidase that is found on the surface of flu viruses.

Still other active agents function by stimulating the patient's immune system. Interferons, including pegylated interferons, are representative compounds of this class. Interferon alpha is used, for example, to treat hepatitis B and C. Various antibodies, including monoclonal antibodies, can also be used to target viruses.

Any of the above-mentioned compounds can be used in combination therapy with the inhibitors described herein.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating viral infections, an effective amount of the inhibitory compound is an amount sufficient to suppress the growth and proliferation of the virus. Viral infections can be prevented, either initially, or from re-occurring, by administering the compounds described herein in a prophylactic manner. Preferably, the effective amount is sufficient to obtain the desired result, but insufficient to cause appreciable side effects.

The effective dose can vary, depending upon factors such as the condition of the patient, the severity of the viral infection, and the manner in which the pharmaceutical composition is administered. The effective dose of compounds will of course differ from patient to patient, but in general includes amounts starting where desired therapeutic effects occur but below the amount where significant side effects are observed.

The compounds, when employed in effective amounts in accordance with the method described herein, are effective at inhibiting the proliferation of certain viruses, but do not significantly effect normal cells.

For human patients, the effective dose of typical compounds generally requires administering the compound in an amount of at least about 1, often at least about 10, and frequently at least about 25 µg/24 hr/patient. The effective dose generally does not exceed about 500, often does not exceed about 400, and frequently does not exceed about 300 µg/24 hr/patient. In addition, administration of the effective dose is such that the concentration of the compound within the plasma of the patient normally does not exceed 500 ng/mL and frequently does not exceed 100 ng/mL.

The invention will be further explained by the following illustrative examples that are intended to be non-limiting.

EXAMPLES

Example 1

Synthesis of Linear tRNA Anticodon Stem Loop Sequences

The first step in producing the fragment tRNA anticodon stem loop (ASL) sequences is the synthesis of the modified nucleotides, also known as phosphoramidites (Agris et. al *Biochimie*. (1995) 77(1-2):125-34). The modified nucleotides are then used during the synthesis of the RNA oligomers (Ogilvie et. al. *Proc Natl Acad Sci USA*. (1988) 85:5764-8). Synthetic approaches overcome the substantial barrier of obtaining sufficient amounts of natural products for the functional characterization studies. In addition to providing the fully modified ASL for characterization of the fragment tRNA:target nucleotide binding, the synthetic approach allows for the preparation of intermediate steps/forms of the modified material that can further elucidate the individual contribution of each modification step in enhanced tRNA binding.

Modified base nucleic acid molecules were prepared using a combination of methods for the synthesis, incorporation, and purification of all the modified nucleotides found in the $ASL^{Lys3}$ human tRNA. Modified base phosphoramidites were prepared using known methods, such as those disclosed in Ogilive et. al., 1988. The $ASL^{Lys3}$ contains 3 modified bases denoted as mcm5s2U, ms2t6A and pseudouridine. Synthesis of the phosphoramides needed for the preparation of the synthetic mimics is described below in detail. Protocols for the polymers synthesis follow those developed for automated RNA synthesis (Ogilive et. al., 1988) with variations specific to the synthesis of the $ASL^{Lys3}$ mimics described below. The description includes methods for the removal of protection group required for automated synthesis and purification of the final products used in the assay.

The protecting group is subsequently removed after synthesis of the RNA oligomer. The addition of a protecting group to each modified base and ribose is described. While 2 position thio-groups can be oxidized in standard RNA synthesis protocols this has been overcome by using the tert-butyl hydroperoxide (10% solution in acetonitrile) oxidizing agent (Kumar and Davis, 1997). These synthetic RNA oligomers have been used in both functional (Yarian 2002 and Phelps 2004) and structural studies (Stuart 2000 and Murphy 2004).

Example IA

The Synthesis of the Protected Monomer Phosphoramidites mcm5s2U

The mcm5s2U nucleoside was prepared following published methods (Reese and Sanghvi 1984). Briefly, 2 thiouridine was heated with 5 molar equivalents each of pyrrolidine and formaldehyde in aqueous solution for 1 h, under reflux, resulting in 2',3'-0isopropylidene-5-pyrrolidinomethyl-2-thiouridine. This base was subsequently treated with 10 molar equivalents of methyl iodide in acetonitrile at room temperature. After 16 hours, the products were concentrated under reduced pressure to give the putative methiodide which was then dissolved in acetonitrile and allowed to react with 3 molar equivalents of glycine t-butyl ester' at room temperature for 16 h. This product was then purified and protection of the ribose and phosphitylation follow the general scheme described below.

ms2t6A

The monomer was obtained by condensation of the 2',3', 5'-O-triacetyl derivative of ms2A with the isocyanate derived from L-threonine-O-t-butyldimethylsilyl (TBDMS)-p-nitrophenylethyl ester, under conditions which eliminate racemization of the amino acid. The product was selectively deprotected at the sugar moiety. Standard procedures were employed for final protection of the 5'-O— and 2'-O-functions with dimethoxytrityl (DMTr) and with TBDMS groups, respectively, as well as for 3'-O-phosphitylation (Agris et al., 1995).

S2U

The thio group was not protected in this synthesis. Protection of the ribose and phosphitylation follow the general scheme in panel C of FIG. 1. Protection of the ribose and phosphitylation follow the general scheme described below.

The sugar-protected phenyl carbamate 6 of t6A nucleoside was synthesized from 1-O-acetyl-2,3,5-tri-O-benzoylribofuranose The carbamate was treated with L-threonine to furnish the sugar-protected t6A nucleoside using the method of Hong and Chheda The remaining synthetic transformations followed general scheme described below.

Example IB

General Procedure for Ribose Protection and Phosphitylation

Methods for the protection of the modified nucleotide bases prior to synthesis of the RNA oligomer are provided (FIG. 1). Panel A of FIG. 1 illustrates protection with trifluoryl acetic acid. Panel B illustrates protection with benzoyl, and panel C illustrates the general protection of the ribose hydroxyl groups.

After base protection the scheme for the synthesis of 5'-O-(4,4'-dimethoxytrityl)-2'-O-tertbutyldimethylsilyi-modified ribonucleoside-3'-O-(2-cyanoethyl-N-diisopropyl)phosphoramidites is the same for both modified nucleotides (Panel C, FIG. 1). The protected nucleoside was dried by co-evaporation twice with pyridine and dissolved in pyridine. Tert-butyldimethylchlorosilane and imidazole were added and reacted for 4 hours at room temperature. The excess silyl chloride was decomposed with water and dichloromethane. The aqueous layer was extracted twice with dichloromethane and combined with the organic layer. The solvent was evaporated by vacuum yielding a gum which is then dissolved in ether and precipitated by pouring slowly into petroleum ether (4060° C.) with stirring. The precipitate was collected and washed twice with petroleum ether. At this point the crude product contains three components; the 2',3' disilylated, 2' silylated (major product) and 3' silylated isomers. The pure 2' protected isomer was purified by silica gel column chromatography. This product is then ready for phosphitylation.

The N-protected-5'-O-dimethoxytrityl-2'-O-tert-butyldimethylsilylribonucleosides were dried by two co-evaporations with anhydrous pyridine and THF. The residue was then dissolved in anhydrous THF under argon. Dimethylaminopyridine, N,N,N-ethyldiisopropylamine and cyano-ethoxydiisopropy amino-chlorophosphine were added through a rubber septum. After 2 hours the reaction mixture, was quenched with ethyl acetate and washed with 5% sodium bicarbonate followed by water. Aqueous washes were back extracted with ethyl acetate. Combined organic layers were dried over sodium sulphate. Solvent was evaporated yielding a viscous oil. The product was co-evaporated twice with toluene and the pale yellow phosphoramidite products were purified by flash silica gel chromatography.

Example IC

Protocols for the Synthesis of the Modified RNA Polymers

The synthesis of the RNA followed standard protocols for a 1 mol scale by solid phase b-cyanoethyl phosphoramidite chemistry with 2'-OTBDMS protection (Usman et al., 1987), and N-4-tbutyl phenoxyacetyl (tac) protection of A, G and C monomers (Sinha et al., 1993). A, G, C and U monomers with tac and 2'-O-TBDMS protection and rC(tac)-succinyl controlled pore glass (CPG) support with the following variations. Addition of the unmodified A, C, G and U monomers were coupled in 5-fold molar excess for 6 min in the presence of 0.3 M 5-(benzylthio)-1H-tetrazole in acetonitrile (Welz and Muller, 2002), whereas mcm5s2U and ms2t6A monomers were used in 3-fold excess and coupled for 10 min. Following the coupling, a 2 min capping was performed with tac anhydride and then a 3 min oxidation with 1M cumene hydroperoxide in toluene. At the end of the synthesis the 5' dimethoxytrityl group was left in place. Example ID: Protocols for the deprotection of the intermediates The deprotection of the RNA was carried out in 3 steps as follows. The argon dried CPG carrying the fully protected RNA was treated with 20 ml of absolutely anhydrous 10% 1,8-diazabicyclo[5.4.0]undec-7-ene (DBU) in tetrahydrofuran for 45 min at 45° C. to beliminate the p-nitrophenylethyl and 2-cyanoethyl protecting groups. The supernatant was removed under a blanket of argon and the CPG was washed twice with dry THF. The CPG carrying partially deprotected RNA was then treated with 20 ml of 10% DBU in dry methanol under argon for 18 h at room temperature to cleave the nucleobase protecting groups and cleave the RNA from the CPG. The supernatant and methanol washings were dried in a Speedvac in a Falcon tube and then dried for 3 days in high vacuum (10)3 Torr) over phosphorus pentaoxide to remove the residual DBU. The 2'-O-TBDMS protected RNA was desilylated using 12 ml of triethylamine trihydrofluoride (Gasparutto et aI., 1992) with vigorous stirring during 24 h at room temperature. During this step the DMT group is also removed from the 5'-terminal G residue. The reaction was quenched by addition of sterile water (1.2 ml) and the crude RNA was precipitated with butanol and kept at 20° C. for 24 h to complete the precipitation. The RNA was collected by centifugation, washed with butanol. Example IE: Purification of the RNA polymers.

The synthetic RNA polymer products are purified by HPLC. The deprotected material is desalted using C18 SEP-PAK and purified by preparative anion-exchange HPLC using a gradient of sodium chloride. In some cases additional purification is required using reverse phase chromatography. To assure that the polymer product is correct it is analyzed by electrospray mass spectroscopy and nucleoside composition analysis.

Example II

Inhibitor Screening Assay

Figure 3:
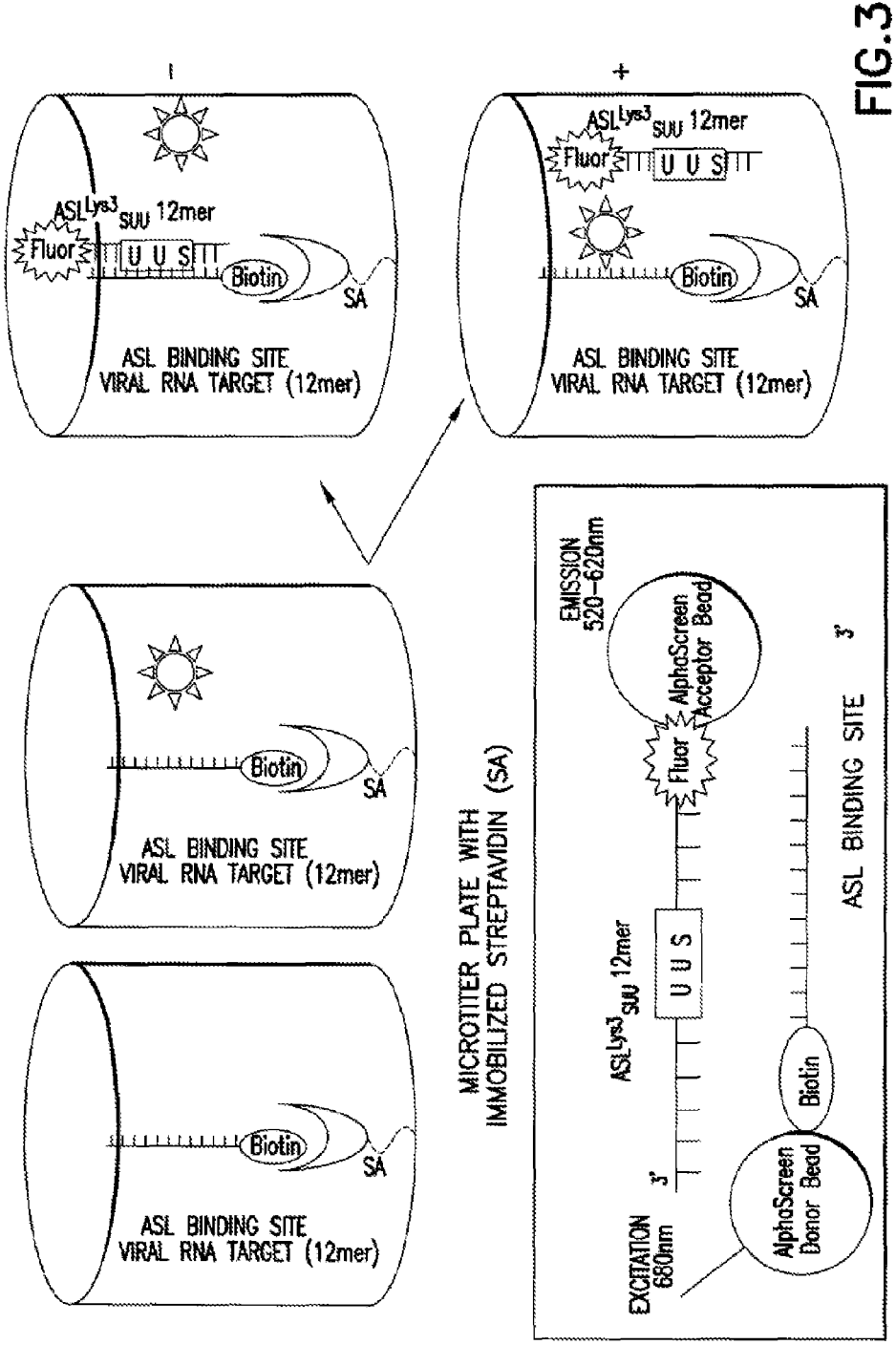
FIG. 3 provides a comparison of one example of an immobilized assay and an assay using the AlphaScreen™ assay.

Two assays were developed using tool and target RNAs, the immobilized assay and the Alphascreen assay (FIG. 3). Both assays use the same two RNA components (the target RNA and the tRNA fragment). In the example, the HIV viral RNA target is a 12mer with a 3' Biotin, while the Human tRNA mimic is a synthetic 12mer containing the native modified nucleotides and 3' fluorescein. These two RNAs mimic an essential complex of the HIV replication complex.

As set forth more fully below, the immobilization assay uses a three step process that first involves the binding of the target RNA to an avidin coated microtiter plate. Then, the test compound (drug/small molecule), denoted as a star, is incubated with the target sequence for 30 min. Then, the tRNA mimic was added to determine if the complex was formed or inhibited. In this assay a phosphate buffer may be used with 1M NaCl to improve the affinity for the two RNA. The stability of the complex is concentration dependent so that µM concentrations are used and the assay is run at 4 degrees C.

The 5' labeled target RNA sequence (5'-CGGU-GUAAAAGC (SEQ ID NO: 5) is bound to a avidin microtiter plate (Roche High Load plates, 96-well avidin microtiter plates) by adding 150 µl of target solution to each well (FIG. 3, step A). The plates are covered and incubated at 37° C. for 1 hour. The plates are then rinsed twice with binding buffer, the second rinse is incubated at 37° C. for 5 minutes. The plates are then rinsed two additional times with binding buffer, covered, and ready for use.

The test compounds were prepared by thawing solutions of the compounds to room temperature. Dilutions of the test compounds (1:10 and 1:500) were prepared by dilution in DMSO and shaking for 1 hour.

The assays were performed by adding 98.5 µl of loading buffer (100 mM Tris HCl, pH 7.5, 150 mM NaCl and 0.1% Tween 20, pH adjusted from around 4.5 to 7.5 with 10 M NaOH) to each well of the plate. Test compounds were added individually to each well (1.5 µl each), and the plates were mixed for 1 hour (FIG. 3, step B).

Fifty microliters of solution containing the tool tRNA (5'-GCUXUUAYZCUG (SEQ ID NO: 1)); where the X, Y, and Z are independently selected from modified nucleosides mnm5s2U, mcm5s2U, ms2t6A, s2U, ψ, and t6A) was then added to each well and the plates were incubated at 4° C. for 1 hour with shaking (FIG. 3, step C). The reaction mixture was then removed, while the mixture was still cold, and the remaining compound solution was also removed.

After removing the remaining solution, reading buffer (50 mM Hepes, pH 7.5, 100 mM NaCl, PEG (40 mg/200 ml)) was then added to each well and the results were read using a plate reader.

As shown in FIG. 3, a positive (+) reaction indicates that the test compound inhibits binding of the tool tRNA to the target nucleic acid (e.g. the test compound binds to either the tool tRNA, the target nucleic acid molecule or both the tool tRNA and the target nucleic acid molecule). A negative (−) reaction indicates that the test compound does not inhibit the binding of the tool tRNA to the target nucleic acid (e.g. the test compound does not bind to either the tool tRNA or the target nucleic acid).

In the AlphaScreen configuration (FIG. 3) the assay is done in solution using the same RNA as the immobilization assay. The donor and acceptor beads are bound to their respective RNA's. During the screening the RNAs and test drugs/small molecules are incubated together and formation of the complex is measured using the AlphaScreen detection conditions. Utilization of the AlphaScreen assay may allow for the assay to be run at a lower RNA concentration at room temperature, and increase the stability of the complex.

Example III

Validation of HIV Screening Assay

The HIV screening assay was validated to confirm that positive and negative controls would function as expected and to test a small compound library to verify that differential inhibition could be detected. Two validation runs were completed with 4,275 and 4,616 compounds, respectively, using 17 plates in each run. There were 3,961 compounds in common between the two assays and the statistical analysis was completed using only these compounds and the positive and negative controls. Each plate contained approximately 30 positive and 30 negative controls and these controls performed as expected. Differences were observed between validation runs when analyzing the luminescence; however, these differences were minimized or eliminated when evaluating the percent inhibition by compounds (hits) that were active in both runs. This assay met the functional requirements based on the results of the positive and negative controls.

To evaluate the inhibition exhibited in the screening of this small compound library, a cutoff was set at 42.96% inhibition, the average plus three times standard deviation of compound percent (%) inhibition. Using this cutoff, 34 repeated compounds (hits) were identified. By using 99.75% inhibition as the cutoff, the average minus three times standard deviation of positive control (Tool+Target) percent (%) inhibition, there is 1 repeated hit. If 29.02%, which is the average plus three times standard deviation of negative control (Tool) percent (%) Inhibition, is defined as the cutoff, there are 51 repeated hits, out of 3961 compounds analyzed. These results are in line with expectations when evaluating a small random compound library.

To select compounds for use in a secondary HIV assay to verify that this assay was capable of identifying HIV specific compounds with biological activity a cutoff was set at greater than 60% inhibition in at least one of the two validations runs. This resulted in the selection of 29 compounds. These compounds were analyzed for anti-HIV activity in freshly harvested PBMC cells. Of the 30 tested compounds, 15 were active at a concentration of less than 100 ~M (the highest tested concentration). Of these 15 compounds, 9 were not toxic to the PBMC cells at the 100 ~M concentration; thus, an absolute conclusion regarding the differential toxicity to HIV and PBMC cells cannot be drawn with these 9 compounds. Two other compounds had an antiviral index (inhibited HIV cells and not PBMC cells) greater than 25 which is acceptable. The two compounds identified were:

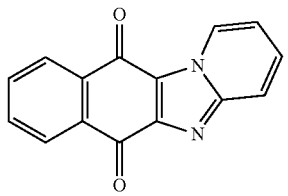 [SMILES: O=C1c2ccccc2C(=O)c2c1nc1ccccn21]

naphtho[2',3',4,5]imidazo[1,2-a]pyridine-6,11-dione; and

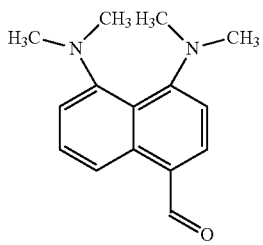

4,5-bis(dimethylamino-1-naphthaldehyde.

Figure 4A:
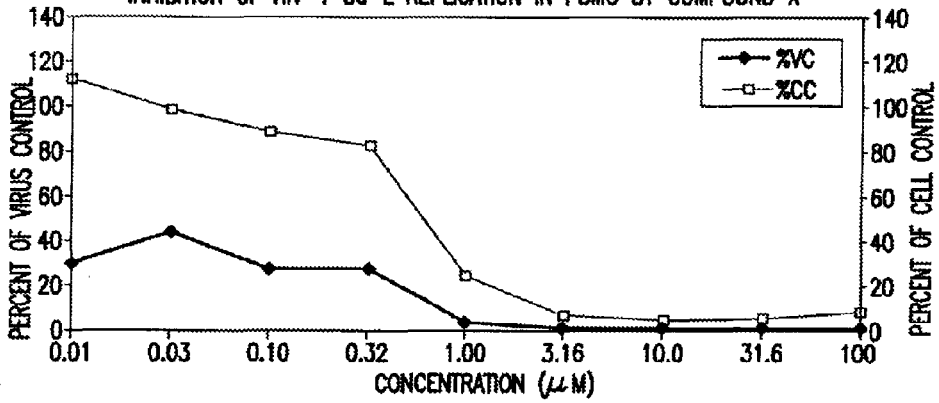
FIGS. 4A and 4B provide tables summarizing data obtained for one compound using an example of the HIV assay.
Figure 4B:
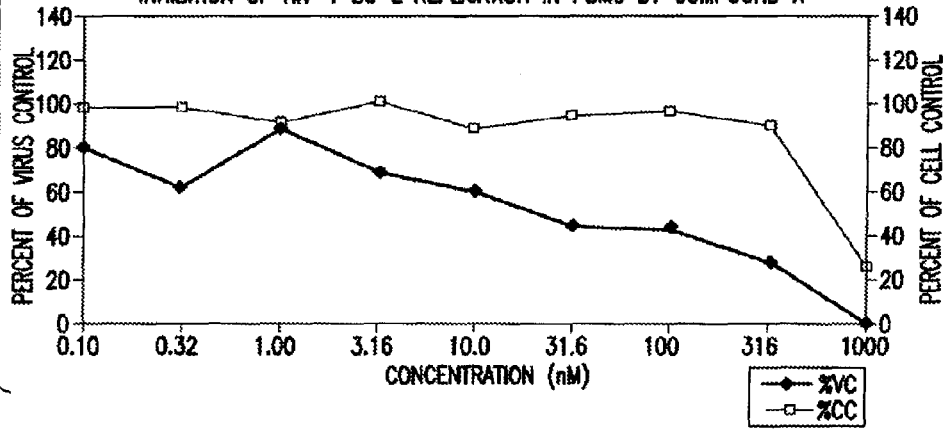
Figure 5:
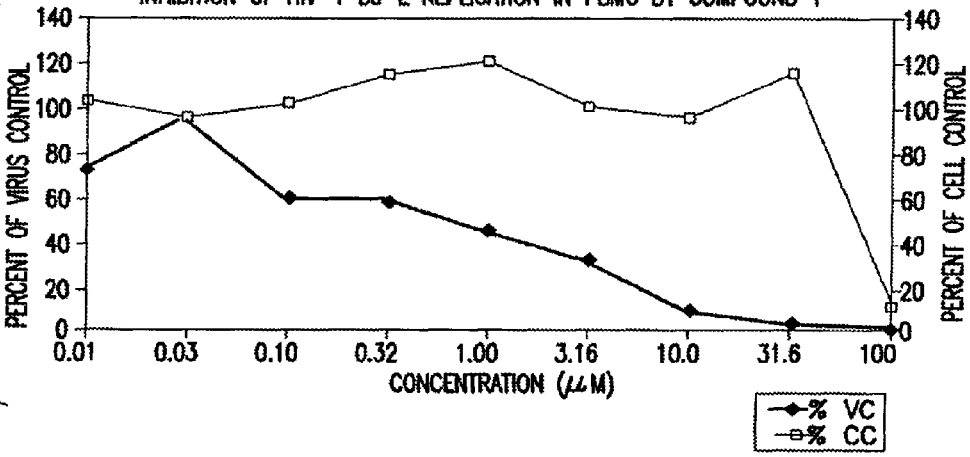
FIG. 5 provides a table summarizing data obtained for a second compound using an example of the HIV assay.
Figure 6:
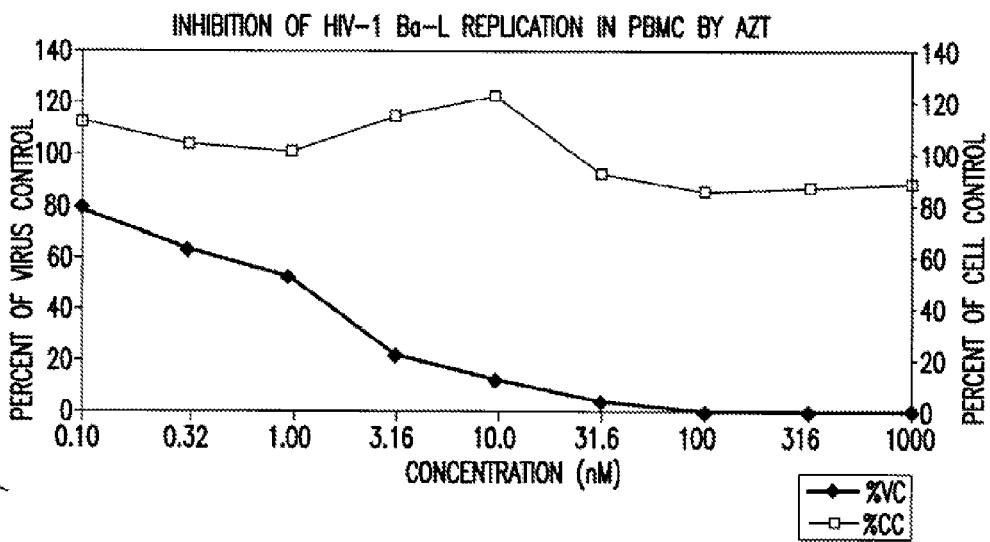
FIG. 6 provides a table summarizing data obtained for a control compound using an example of the HIV assay.

The two compounds demonstrated anti-HIV activity at 0.63 and 0.022 µM and had an antiviral index greater than 25. One compound was inactive in the reverse transcriptase assay indicating that the compound does not inhibit this enzyme and indicating that the compound inhibits the RNA:RNA interaction that the assay is designed to mimic. The results of the assays for the two compounds and a control compound are presented in FIGS. 4, 5, and 6.

Although the foregoing invention has been described in some detail by way of illustration and example for purposes of clarity of understanding, it will be obvious that certain changes and modifications may be practiced within the scope of the appended claims.

What is claimed is:

1. A method of identifying an anti-HIV agent, comprising:
   forming a mixture comprising:
   a linear sequence of a tRNA anticodon stem loop (ASL) fragment that is not capable of forming a stem-loop, and comprising the sequence 5'-GCUXUUAYZCUG (SEQ ID NO: 1), in which the X, Y, and Z refer to modified nucleosides, and optionally comprises a label;
   a target nucleic acid molecule capable of binding to the tRNA anticodon stem loop fragment, and
   a test compound,
   wherein the target nucleic acid molecule comprises residues 157 to 169 of the 5' untranslated region of HIV-1;
   incubating the mixture under conditions that allow binding of the tRNA anticodon stem loop fragment and the target nucleic acid molecule in the absence of the test compound; and
   detecting whether or not the test compound inhibits the binding of the tRNA anticodon stem loop fragment and the target nucleic acid molecule, wherein the absence of binding of the tRNA ASL fragment and the target nucleic acid molecule is indicative of the test compound being:
   i) an inhibitor of retroviral propagation.

2. The method of claim 1, wherein the modified nucleosides are selected from the group consisting of I-methyladenosine (m1A), 2-methyladenosine (m2A), N6-isopentenyladenosine (i6A), 2-methylthio-N6-isopentenyladenosine (ms2i6A), N6-methyladenosine (m6A), N6-threonylcarbamoyladenosine (t6A), N6-methyl-N6threonylcarbomoyladenosine (m6t6A), 2-methylthio-N6-threonylcarbamoyladenosine (ms2t6A), 2'-O-methyladenosine I Inosine (Am), I-methylinosine Ar(p) 2'-O-(5-phospho)ribosyladenosine (m1I), N6-(cis-hydroxyisopentenyl)adenosine (i06A), 2-thiocytidine (s2C), 2'-O-methylcytidine (Cm), N4-acetylcytidine (ac4C), 5-methylcytidine (m5C), 3-methyl cytidine (m3C), lysidine (k2C), 5-forml1cytidin (f5C), 2'-O-methyl-5-formylcytidin (f5Cm), 2'-O-(5phospho) ribosylguanosine (Gr(p)), I-methylguanosine (mIG), N2-methylguanosine (m2G), 2'-O-methylguanosine (Gm), N2 N2-dimethylguanosine (m22G), N2,N2,2'-O -trimethylguanosine (m22Gm), 7-methylguanosine (m7G), archaeosine (fa7d7G), queuosine (Q), mannosylqueuosine (manQ), galactosyl-queuosine (galQ), wybutosine (yW), peroxywybutosine (O2yW), 5-methylaminomethyluridine (mnm5U), 2-thiouridine (s2U), 2'-O-methyluridine (Urn), 4-thiouridine (s4U), 5-carbamoylmethyluridine (ncm5U), 5-methoxycarbonylmethyluridine (mcm5U), 5-methylaminomethyl-2-thiouridine (mnm5s2U), 5-methoxycarbonylmethyl-2-thiouridine (mcm5s2U), uridine 5-oxyacetic acid (cmO5U), 5-methoxyuridine (mo5U), 5-carboxymethylaminomethyluridine (cmnm5U), 5-carboxymethylaminomethyl-2-thiouridine (cmnm5s2U), 3-(3-amino-3-carboxypropyl)uridine (acp3U), 5(carboxyhydroxymethyl)uridinemethyl ester (mchm5U), 5-carboxymethylaminomethyl-2'-O-methyluridine (cmnm5Um), 5-carbamoylmethyl-2'-O- methyluridine (ncm5Um), Dihydrouridine (D), pseudouridine (ψ), 1-methylpseudouridine (m1Ψ), 2'-O-methylpseudouridine (ψm), ribosylthymine (m5U), 5-methyl-2-thiouridine (m5s2U), and 5,2'-O-dimethyluridine (m5Um).

3. The method of claim 1, wherein the modified nucleosides are selected from the group consisting of mnm5s2U, mcm5s2U, ms2t6A, s2U, ψ, and t6A.

4. The method of claim 1, wherein the tRNA anticodon stem loop fragment comprises the nucleic acid sequence 5'-CU(mnm5s2U)UU(ms2t6A)A(ψ)CUGC (SEQ ID NO: 2), GCU(mnm5s2U)UU(ms2t6A)A(ψ)CUG (SEQ ID NO: 3) or CU(mnm5s2U)UU(ms2t6A)A(ψ)CUGC(fluorescein).

5. The method of claim 1, wherein the tRNA anticodon stem loop fragment consists essentially of the nucleic acid sequence 5'-CU(mnm5s2U)UU(ms2t6A)A(ψ)CUGC(fluorescein).

6. The method of claim 1, wherein the tRNA anticodon stem loop fragment is a linear fragment having from 10 to 14 nucleotides.

7. The method of claim 1, wherein the mixture forming step includes the addition of one or more test compounds to the mixture.

8. The method of claim 1, wherein the tRNA fragment further comprises a label.

9. The method of claim 8, wherein the label is selected from the group consisting of affinity tags, radioactive isotopes, dyes, fluorescent, fluorophores, electron-dense reagents, enzymes and their substrates, biotin-streptavidin, digoxigenin, or hapten; and proteins and antisera or monoclonal antibodies which bind to the proteins.

10. The method of claim 8, further comprising contacting an isolated anticodon stem loop tRNA fragment, wherein the tRNA fragment comprises a label and the label is an affinity tag, with a complimentary ligand coupled to a solid support that allows for the capture of the affinity tag-labeled tRNA fragment.

11. The method of claim 10, wherein the affinity tags and complementary partners are selected from the group consisting of biotin-streptavidin, complementary nucleic acid fragments, aptamers, or haptens and proteins for which antisera or monoclonal antibodies are available.

12. A method of screening for inhibitors of retroviral propagation, comprising:
   a) obtaining
      i) a mixture containing:
         a linear sequence of a tRNA anticodon stem loop (ASL) fragment,
         a target nucleic acid molecule which comprises residues 157 to 169 of the 5' untranslated region of HIV-1, and capable of binding to the tRNA anticodon stem loop fragment to form a complex,
         a donor or acceptor bead that binds to the anticodon stem loop fragment while not affecting the fragments ability to bind to the target nucleic acid molecule;
         an acceptor or donor bead capable of binding to the target nucleic acid molecule and containing a detection signal enhancer to amplify the signal induced by binding of the tRNA anticodon stem loop fragment and the target nucleic acid molecule, and the associated interaction between the acceptor and donor beads on the tRNA anticodon stem loop fragment and the target nucleic acid molecule, and
      ii) a test compound,
   b) incubating the target nucleic acid molecule in the mixture under conditions that allow binding of the tRNA anticodon stem loop fragment and the target nucleic acid molecule in the absence of the test compound; and
   c) detecting whether or not the test compound binds to the tRNA ASL fragment or the target nucleic acid molecule,
   wherein the binding is indicative of the test compound being an inhibitor of the propagation of a retrovirus,
   wherein a positive determination is made by the detection of change in a spectral signal that is the result of disruption of the complex formation, and
   wherein the tRNA anticodon stem loop fragment comprises the sequence 5'-GCUXUUAYZCUG (SEQ ID NO: 1), in which the X, Y, and Z refer to modified nucleosides, and optionally comprises a label.

13. The method of claim 12, wherein the modified nucleosides are selected from the group consisting of I-methyladenosine (m1A), 2-methyladenosine (m2A), N6-isopentenyladenosine (i6A), 2-methylthio-N6-isopentenyladenosine (ms2i6A), N6-methyladenosine (m6A), N6-threonylcarbamoyladenosine (t6A), N6-methyl-N6 threonylcarbomoyladenosine (m6t6A), 2-methylthio-N6-threonylcarbamoyladenosine (ms2t6A), 2'-O-methyladenosine I Inosine (Am), I-methylinosine Ar(p) 2'-O-(5-phospho)ribosyladenosine (m1I), N6-(cis-hydroxyisopentenyl)adenosine (i06A), 2-thiocytidine (s2C), 2'-O-methylcytidine (Cm), N4-acetylcytidine (ac4C), 5-methylcytidine (m5C), 3-methylcytidine (m3C), lysidine (k2C), 5-form11cytidin (f5C), 2'-O-methyl-5-formylcytidin (f5Cm), 2'-O-(5phospho) ribosylguanosine (Gr(p)), I-methylguanosine (mIG), N2-methylguanosine (m2G), 2'-O-methylguanosine (Gm), N2 N2-dimethylguanosine (m22G), N2,N2,2'-O-trimethylguanosine (m22Gm), 7-methylguanosine (m7G), archaeosine (fa7d7G), queuosine (Q), mannosyl-queuosine (manQ), galactosyl-queuosine (galQ), wybutosine (yW), peroxywybutosine (O2yW) 5-methylaminomethyluridine (mnm5U), 2-thiouridine (s2U), 2'-O-methyluridine (Urn), 4-thiouridine (s4U), 5-carbamoylmethyluridine (ncm5U), 5-methoxycarbonylmethyluridine (mcm5U), 5-methylaminomethyl-2-thiouridine (mnm5s2U), 5-methoxycarbonylmethyl-2-thiouridine (mcm5s2U), uridine 5-oxyacetic acid (cmO5U), 5-methoxyuridine (mo5U), 5-carboxymethylaminomethyluridine (cmnm5U), 5-carboxymethylaminomethyl-2-thiouridine (cmnm5s2U), 3-(3-amino-3-carboxypropyl)uridine (acp3U), 5(carboxyhydroxymethyl)uridinemethyl ester (mchm5U), 5-carboxymethylaminomethyl-2'-O-methyluridine (cmnm5Um), 5-carbamoylmethyl-2'-O-methyluridine (ncm5Um), Dihydrouridine (D), pseudouridine (ψ), 1-methylpseudouridine (m1ψ), 2'-O-methylpseudouridine (ψm), ribosylthymine (m5U), 5-methyl-2-thiouridine (ψm5s2U), and 5,2'-O-dimethyluridine (m5Um).

14. The method of claim 12, wherein the modified nucleosides are selected from the group consisting of mnm5s2U, mcm5s2U, ms2t6A, s2U, ψ, and t6A.

15. The method of claim 12, wherein the tRNA anticodon stem loop fragment comprises the nucleic acid sequence 5'-CU(mnm5s2U)UU(ms2t6A)A(ψ)CUGC (SEQ ID NO: 2), GCU(mnm5s2U)UU(ms2t6A)A(ψ)CUG (SEQ ID NO: 3) or CU(mnms2U)UU(ms2t6A)A(ψ)CUGC(fluorescein).

16. The method of claim 12, wherein the tRNA anticodon stem loop fragment consists essentially of the nucleic acid sequence 5'-CU(mnm5s2U)UU(ms2t6A)A(ψ)CUGC(fluorescein).

17. The method of claim 12, wherein the tRNA anticodon stem loop fragment is a linear fragment having from 10 to 14 nucleotides.

18. The method of claim 12, wherein the mixture forming step includes the addition of one or more test compounds to the mixture.

19. The method of claim 12, wherein the tRNA fragment further comprises a label.

20. The method of claim 19, wherein the label is selected from the group consisting of affinity tags, radioactive isotopes, dyes, fluorescent, fluorophores, electron-dense reagents, enzymes and their substrates, biotin-streptavidin, digoxigenin, or hapten; and proteins and antisera or monoclonal antibodies which bind to the proteins.

21. The method of claim 19, further comprising contacting an isolated anticodon stem loop tRNA fragment, wherein the tRNA fragment comprises a label and the label is an affinity tag, with a complimentary ligand coupled to a solid support that allows for the capture of the affinity tag-labeled tRNA fragment.

22. The method of claim 21, wherein the affinity tags and complementary partners are selected from the group consisting of biotin-streptavidin, complementary nucleic acid fragments, aptamers, or haptens and proteins for which antisera or monoclonal antibodies are available.

* * * * *

SEQUENCE LISTING

```
<160> NUMBER OF SEQ ID NOS: 5

<210> SEQ ID NO 1
<211> LENGTH: 12
<212> TYPE: RNA
<213> ORGANISM: Artificial Sequence
<220> FEATURE:
<223> OTHER INFORMATION: tRNA anticodon stem loop fragment
<220> FEATURE:
<221> NAME/KEY: misc_feature
<222> LOCATION: (4)..(4)
<220> FEATURE:
<221> NAME/KEY: misc_feature
<222> LOCATION: (4)..(4)
<223> OTHER INFORMATION: modified or unmodified nucleoside
<220> FEATURE:
<221> NAME/KEY: misc_feature
<222> LOCATION: (8)..(8)
<223> OTHER INFORMATION: modified or unmodified nucleoside
<220> FEATURE:
<221> NAME/KEY: misc_feature
<222> LOCATION: (9)..(9)
<223> OTHER INFORMATION: modified or unmodified nucleoside

<400> SEQUENCE: 1
gcunuuannc ug                                                    12
```

```
<210> SEQ ID NO 2
<211> LENGTH: 12
<212> TYPE: RNA
<213> ORGANISM: Artificial Sequence
<220> FEATURE:
<223> OTHER INFORMATION: tRNA anticodon stem loop fragment
<220> FEATURE:
<221> NAME/KEY: modified_base
<222> LOCATION: (3)..(3)
<223> OTHER INFORMATION: 5-methylaminomethyl-2-thiouridine
<220> FEATURE:
<221> NAME/KEY: modified_base
<222> LOCATION: (6)..(6)
<223> OTHER INFORMATION: 2-methylthio-N6-threonylcarbamoyladenosine
<220> FEATURE:
<221> NAME/KEY: modified_base
<222> LOCATION: (8)..(8)
<223> OTHER INFORMATION: pseudouridine

<400> SEQUENCE: 2
cuuuuaaucu gc                                                          12

<210> SEQ ID NO 3
<211> LENGTH: 12
<212> TYPE: RNA
<213> ORGANISM: Artificial Sequence
<220> FEATURE:
<223> OTHER INFORMATION: tRNA anticodon stem loop fragment
<220> FEATURE:
<221> NAME/KEY: modified_base
<222> LOCATION: (4)..(4)
<223> OTHER INFORMATION: 5-methylaminomethyl-2-thiouridine
<220> FEATURE:
<221> NAME/KEY: modified_base
<222> LOCATION: (7)..(7)
<223> OTHER INFORMATION: 2-methylthio-N6-threonylcarbamoyladenosine
<220> FEATURE:
<221> NAME/KEY: modified_base
<222> LOCATION: (9)..(9)
<223> OTHER INFORMATION: pseudouridine

<400> SEQUENCE: 3
gcuuuuaauc ug                                                          12

<210> SEQ ID NO 4
<211> LENGTH: 12
<212> TYPE: RNA
<213> ORGANISM: Artificial Sequence
<220> FEATURE:
<223> OTHER INFORMATION: fragment of 5' untranslated region of HIV-1

<400> SEQUENCE: 4
gcgguguaaa ag                                                          12

<210> SEQ ID NO 5
<211> LENGTH: 12
<212> TYPE: RNA
<213> ORGANISM: Artificial Sequence
<220> FEATURE:
<223> OTHER INFORMATION: fragment of 5' untranslated region of HIV-1

<400> SEQUENCE: 5
cgguguaaaa gc                                                          12
```